United States Patent
Pettis et al.

(10) Patent No.: US 8,900,186 B2
(45) Date of Patent: *Dec. 2, 2014

(54) MICRONEEDLE-BASED PEN DEVICE FOR DRUG DELIVERY AND METHOD FOR USING SAME

(75) Inventors: Ronald J. Pettis, Cary, NC (US); Frank E. Martin, Durham, NC (US); Scott A. Kaestner, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 834 days.

This patent is subject to a terminal disclaimer.

(21) Appl. No.: 12/379,078

(22) Filed: Feb. 12, 2009

(65) Prior Publication Data

US 2009/0157041 A1 Jun. 18, 2009

Related U.S. Application Data

(63) Continuation of application No. 10/238,958, filed on Sep. 11, 2002, now Pat. No. 7,556,615.

(60) Provisional application No. 60/318,913, filed on Sep. 12, 2001, provisional application No. 60/318,886, filed on Sep. 12, 2001.

(51) Int. Cl.
| | |
|---|---|
| *A61M 5/00* | (2006.01) |
| *A61M 5/28* | (2006.01) |
| *A61M 5/315* | (2006.01) |
| *A61M 5/32* | (2006.01) |
| *A61M 37/00* | (2006.01) |
| *A61M 5/20* | (2006.01) |
| *A61M 5/42* | (2006.01) |

(52) U.S. Cl.
CPC .............. *A61M 5/28* (2013.01); *A61M 5/31593* (2013.01); *A61M 5/32* (2013.01); *A61M 2037/003* (2013.01); *A61M 5/20* (2013.01); *A61M 5/3298* (2013.01); *A61M 37/0015* (2013.01); *A61M 5/31568* (2013.01); *A61M 2037/0023* (2013.01); *A61M 5/425* (2013.01); *A61M 5/31548* (2013.01)
USPC ............ 604/117; 604/115; 604/205; 604/272

(58) Field of Classification Search
CPC ................... A61M 2005/2474; A61M 5/3293; A61M 5/3295; A61M 5/3298; A61M 5/46; A61M 37/0015; A61M 2037/003
USPC ......... 604/115, 117, 181, 183, 187, 200, 201, 604/205, 206, 411–4, 272
See application file for complete search history.

(56) References Cited

U.S. PATENT DOCUMENTS 3,596,660 A * 8/1971 Melone ........................... 604/47
3,739,779 A    6/1973 Pfleger
(Continued)

FOREIGN PATENT DOCUMENTS

EP          1 092 444 B1     5/2006
WO          WO 94/23777      10/1994
(Continued)

*Primary Examiner* — Aarti B Berdichevsky
*Assistant Examiner* — Laura Schell
(74) *Attorney, Agent, or Firm* — Roylance, Abrams, Berdo and Goodman, LLP

(57) ABSTRACT

A system and method is provided for an injectable substance delivery pen comprising a microneedle hub assembly removably engaged with a pen device body which includes a cartridge, a plunger, and a drive mechanism. The hub assembly includes at least one microneedle for intradermal or shallow subcutaneous injection of the contents of the cartridge. The cartridge, plunger and drive mechanism components of the pen body are fabricated of non-compliant and non-compressible materials to allow effective communication of the cartridge contents via the microneedle patient interface.

5 Claims, 7 Drawing Sheets

(56) References Cited

U.S. PATENT DOCUMENTS

| | | | |
|---|---|---|---|
| 3,797,490 A | 3/1974 | Hurschman et al. | |
| 3,884,229 A * | 5/1975 | Raines et al. | 604/205 |
| 3,964,482 A | 6/1976 | Gerstel et al. | |
| 4,373,526 A | 2/1983 | Kling | |
| 4,409,991 A | 10/1983 | Eldridge | |
| 4,518,387 A | 5/1985 | Murphy et al. | |
| 4,583,978 A | 4/1986 | Porat et al. | |
| RE32,974 E | 7/1989 | Porat et al. | |
| 5,078,691 A | 1/1992 | Hamacher | |
| 5,147,311 A | 9/1992 | Pickard | |
| 5,199,473 A | 4/1993 | Galloway | |
| 5,279,544 A | 1/1994 | Gross et al. | |
| 5,281,198 A | 1/1994 | Haber et al. | |
| 5,314,412 A | 5/1994 | Rex | |
| 5,378,233 A | 1/1995 | Haber et al. | |
| 5,505,694 A | 4/1996 | Hubbard et al. | |
| 5,514,097 A | 5/1996 | Knauer | |
| 5,599,323 A | 2/1997 | Bonnichsen et al. | |
| 5,820,622 A | 10/1998 | Gross et al. | |
| 5,951,530 A | 9/1999 | Steengaard et al. | |
| 5,984,906 A | 11/1999 | Bonnichsen et al. | |
| 6,190,367 B1 | 2/2001 | Hall | |
| 6,203,529 B1 | 3/2001 | Gabriel et al. | |
| 6,312,612 B1 | 11/2001 | Sherman et al. | |
| 6,364,865 B1 | 4/2002 | Lavi et al. | |
| 6,379,324 B1 | 4/2002 | Gartstein et al. | |
| 6,494,865 B1 | 12/2002 | Alchas | |
| 6,537,242 B1 | 3/2003 | Palmer | |
| 6,558,402 B1 | 5/2003 | Chelak et al. | |
| 6,569,143 B2 | 5/2003 | Alchas et al. | |
| 6,589,209 B1 | 7/2003 | Dysarz | |
| 6,743,211 B1 | 6/2004 | Prausnitz et al. | |
| 6,843,783 B2 * | 1/2005 | Ooyauchi | 604/239 |
| 6,942,645 B2 | 9/2005 | Alexandre et al. | |
| 7,014,615 B2 * | 3/2006 | Erickson et al. | 600/573 |
| 7,186,222 B1 | 3/2007 | Callister et al. | |
| 7,556,615 B2 * | 7/2009 | Pettis et al. | 604/117 |
| 2001/0056263 A1 | 12/2001 | Alchas et al. | |
| 2002/0038111 A1 | 3/2002 | Alchas et al. | |
| 2002/0045858 A1 * | 4/2002 | Alchas et al. | 604/117 |
| 2002/0068909 A1 | 6/2002 | Alchas et al. | |
| 2002/0156453 A1 | 10/2002 | Pettis et al. | |
| 2002/0193740 A1 | 12/2002 | Alchas et al. | |
| 2002/0193778 A1 | 12/2002 | Alchas et al. | |
| 2002/0198509 A1 | 12/2002 | Mikszta et al. | |
| 2003/0050602 A1 | 3/2003 | Pettis et al. | |
| 2003/0181863 A1 | 9/2003 | Ackley et al. | |
| 2005/0065472 A1 | 3/2005 | Cindrich et al. | |
| 2005/0187519 A1 | 8/2005 | Harris et al. | |
| 2006/0229562 A1 | 10/2006 | Marsh et al. | |
| 2006/0229570 A1 | 10/2006 | Lovell et al. | |

FOREIGN PATENT DOCUMENTS

| | | |
|---|---|---|
| WO | WO 97/48440 | 12/1997 |
| WO | WO 97/48441 | 12/1997 |
| WO | WO 97/48442 | 12/1997 |
| WO | WO 02-02179 A1 | 1/2002 |
| WO | WO 2004-108193 A1 | 12/2004 |
| WO | WO 2005-025641 A2 | 3/2005 |

* cited by examiner

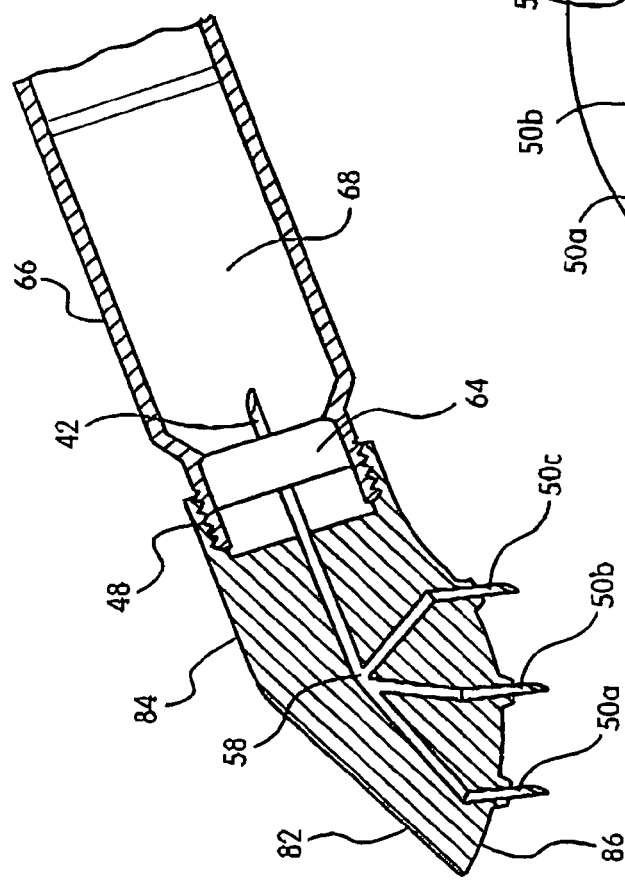
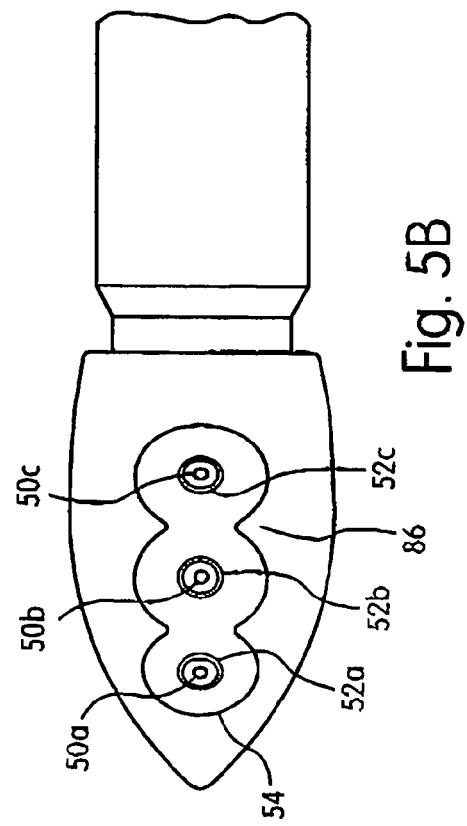
Fig. 5A
Fig. 5B

MICRONEEDLE-BASED PEN DEVICE FOR DRUG DELIVERY AND METHOD FOR USING SAME

CROSS-REFERENCE TO RELATED APPLICATIONS

This application is a continuation of U.S. patent application Ser. No. 10/238,958, entitled "Microneedle-Based Pen Device For Drug Delivery And Method For Using Same", filed Sep. 11, 2002, now U.S. Pat. No. 7,556,615, which claims the benefit of U.S. Provisional Patent Application No. 60/318,913, entitled "Microneedle-Based Pen Devices For Drug Delivery", filed Sep. 12, 2001, and U.S. Provisional Patent Application No. 60/318,886, entitled "Microneedle-Based Pen Devices For Drug Delivery And Method", also filed Sep. 12, 2001, all three of said applications being incorporated herein by reference.

FIELD OF THE INVENTION

The present invention relates generally to substance delivery pen devices. Specifically, the invention relates to an injection pen device and method that incorporates microneedle systems for the user interface.

BACKGROUND OF THE INVENTION

Currently, several pen systems are available for subcutaneous substance delivery. These pen systems typically use 31 gauge needles having a length of about 8 mm and are used to deliver the contents of a cartridge, such as insulin, to patients rapidly and as painlessly as possible. Additional details of intradermal drug delivery have been previously described in U.S. patent application Ser. No. 09/835,243, filed Apr. 13, 1999, and Ser. No. 09/417,671 filed Oct. 14, 1999, the entire content of each application being incorporated herein by reference.

Although currently available pen systems utilize designs manufactured to maximize patient comfort, a need exists for a "microneedle" pen system which can offer an inherent advantage in the reduced pain and sensation to the user resulting from the minimal penetration associated with the extremely small microneedles used. Such microneedle drug delivery systems however, require shorter needles, typically less than or equal to 3 mm, and smaller diameters of 34 gauge or less. Such needle lengths and gauges are required due to depth constraints and bevel edge openings, which are required to access only the deep intradermal or shallow subcutaneous tissue space. Simple modification of current pen systems used for subcutaneous delivery is not possible because of severe engineering constraints associated with the size and volume restrictions imposed by the use of microneedles.

Therefore, a need exists to provide a system and method for the incorporation of microneedle systems as the pen outlet, or user interface. As this results in significant changes in the in vitro and in vivo function of the pen system, additional engineering requirements and methods of use are also required for the effective function of the pen device.

SUMMARY OF THE INVENTION

An object of the present invention is to provide an injection pen device that incorporates microneedle systems for the user interface.

Another object of the present invention is to provide an injection pen device which has a sufficiently open fluid path to allow ready transport of a liquid or suspension from a cartridge to a microneedle inlet, without requiring excessive pressure or occlusion.

Another object of the present invention is to provide an injection pen device which has a biological interface composed of one or more hollow cannula which can penetrate the stratum corneum and accurately access the desired tissue depth in skin or in the proximity of skin.

Another object of the present invention is to provide an injection pen device which has a biological interface that can transmit a desired fluid volume through the body of the interface into a specified or targeted tissue depth both accurately, with no fluid loss out of tissue to surface or to untargeted tissue, and efficiently, in a manner that is amenable to the device user and recipient.

Another object of the present invention is to provide an injection pen device which has a fluid delivery mechanism that can provide the high pressures necessary for fluid delivery to the dermal or near dermal space, withstand pressure and compression, inherent in the fluid delivery to the targeted tissue space, and is easily activated by the user to deliver the fluid.

Another object of the present invention is to provide an injection pen device which can be maintained in an orientation or configuration with respect to the patient's skin for a sufficient time period to accomplish delivery.

These and other objects are substantially achieved by providing a system and method for a substance delivery pen device which includes a hub assembly, removably engaged with a pen body housing containing a cartridge for holding a substance to be delivered, and a non-compliant and non-compressible plunger at one end of the cartridge driven by a drive mechanism.

The hub assembly has at least one microneedle suitable for deep intradermal or shallow subcutaneous injection of a substance, and a fluid channel suitable for connecting the microneedle and the cartridge. Activation of the drive mechanism causes pressure to be exerted on the plunger in contact with the cartridge causing the contents of the cartridge to flow from the cartridge, through the fluid channel and the at least one microneedle, and into the deep dermal or shallow subcutaneous region of the patient.

The hub assembly can include a microneedle array having one or more microneedles as required by the application and can removably engage the pen body housing through, for example, a threaded assembly or a Luer lock. The hub assembly can further include a mechanism for skin tensioning during or before use of the pen device. The tensioning mechanism can include a number of member combinations, including skin tensioning rings and depth limiting posts located on the skin contact surface of the hub assembly. The hub assembly further includes a mechanism, such as a back-end needle, for piercing the septum of the cartridge, and receiving the contents as driven by the plunger. The plunger can be, for example, a rod or circular screw drive, engaged with an actuator used to exert pressure on the plunger through a linear screw drive, a ratcheting means, a spring, air pressure or other mechanical means.

Further objectives and advantages, as well as the structure and function of preferred embodiments will become apparent from a consideration of the following description, drawings and examples.

BRIEF DESCRIPTION OF THE DRAWINGS

These and other objects, advantages and novel features of the invention will be more readily appreciated from the following detailed description when read in conjunction with the accompanying drawings, in which:

FIG. 5A is a view illustrating a substance delivery pen according to a second embodiment of the present invention;

FIG. 5B is a bottom view illustrating a substance delivery pen of FIG. 5A;

In the drawing figures, it will be understood that like numerals refer to like structures.

DETAILED DESCRIPTION OF THE PREFERRED EMBODIMENTS

For pen delivery devices, various microneedle systems can be incorporated to function both as the drug outlet and the biological interface with the patient or end-user. In the embodiments of the present invention described below, the microdevice pen device includes a single or multineedle-array pen needle head, or hub assembly, that is used as a simple screw-on attachment, adaptable to a variety of currently manufactured pen devices.

The embodiments also incorporate a post and ring configuration in which each cannula of the hub assembly protrudes from a member, such as a post, surrounded by a valley, and is then circumscribed by an additional member, or ring of a height relative to the internal post. This arrangement assists in skin tensioning, limits needle penetration, and allows an area for formation of the intradermal bleb or wheal during injection.

The embodiments also include an improved drug cartridge, which minimizes elastomeric compression through the use of a polytetrafluoroethylene, or PTFE stopper. The embodiments include an improved drive mechanism which further decreases elastomeric compression, increases mechanical advantage, accuracy and perception of individual unit increments, and generates end-of-dose locking capabilities. Still other embodiments utilize improved drive or compression mechanisms.

Figure 1A:
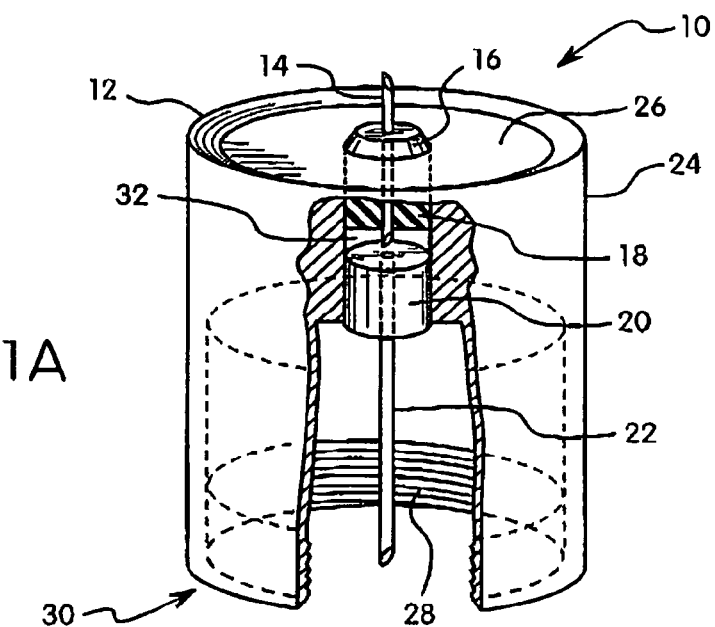
FIG. 1A is a perspective view illustrating an example of a single microneedle hub assembly according to an embodiment of the present invention.
Figure 1B:
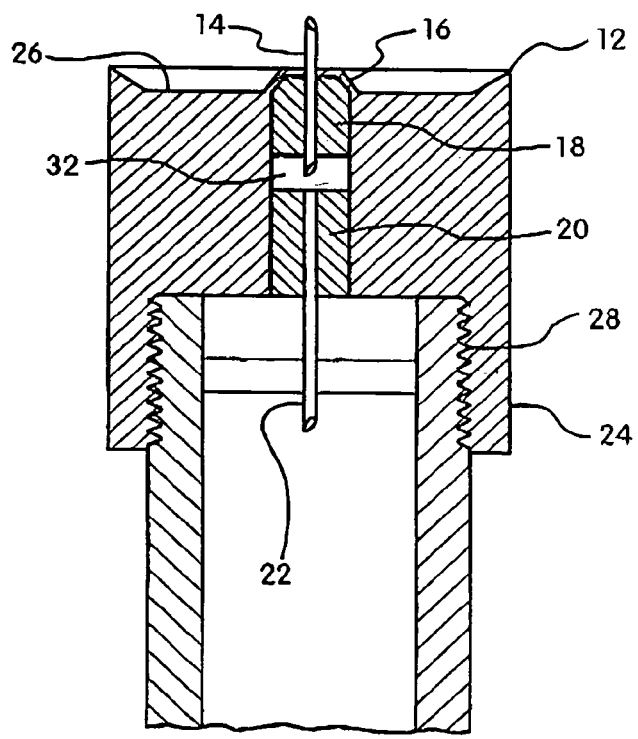
FIG. 1B is a side view in cross section illustrating an example of a single microneedle hub assembly of FIG. 1A.
Figure 2A:
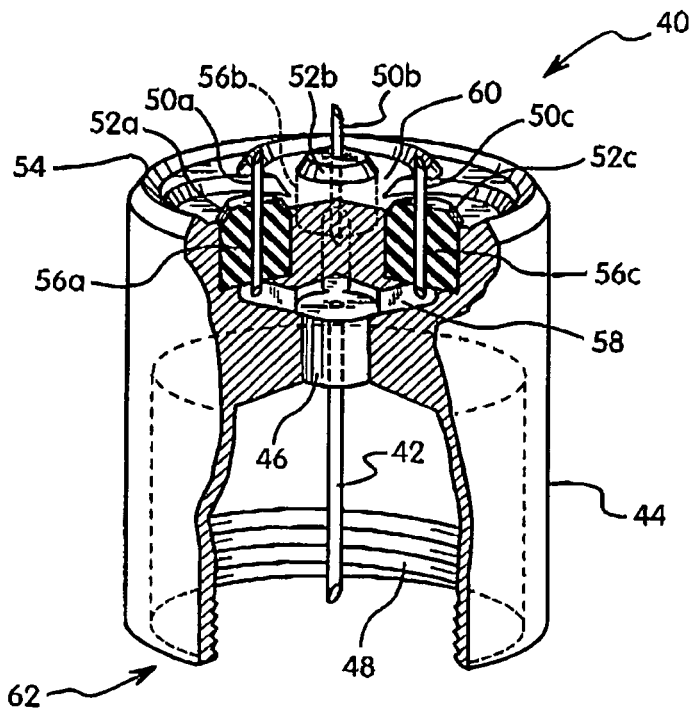
FIG. 2A is a perspective view illustrating an example of a multiple microneedle hub assembly according to an embodiment of the present invention.
Figure 2B:
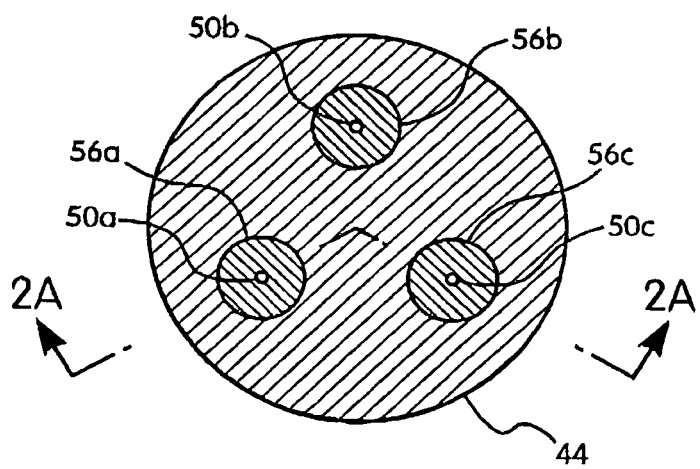
FIG. 2B is a first top view in cross section illustrating an example of a multiple microneedle hub assembly of FIG. 2A.
Figure 2C:
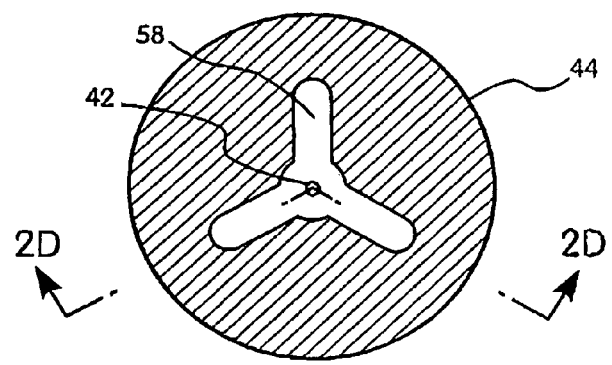
FIG. 2C is a second top view in cross section illustrating an example of a multiple microneedle hub assembly of FIG. 2A.
Figure 2D:
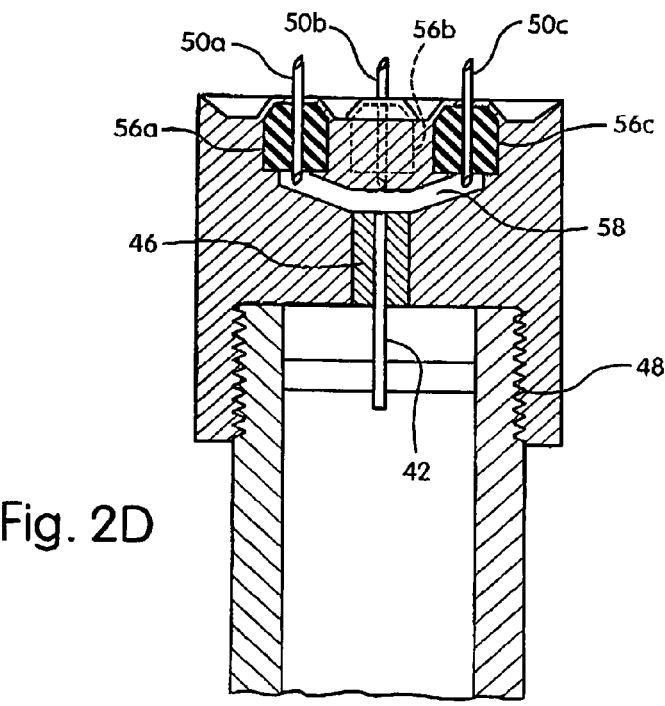
FIG. 2D is a side view in cross section illustrating an example of a multiple microneedle hub assembly of FIG. 2A.
Figure 3B:
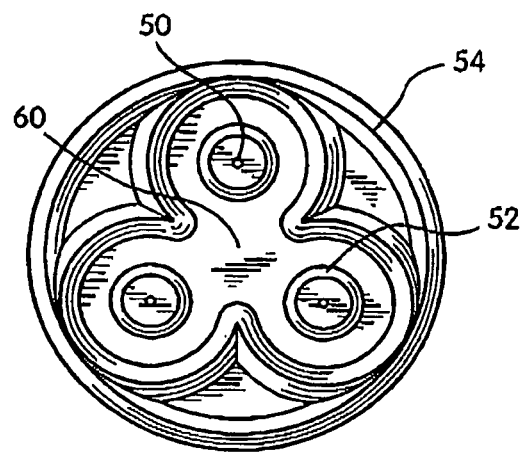
FIG. 3B is a top view of the multiple microneedle hub assembly of FIG. 2.
Figure 3A:
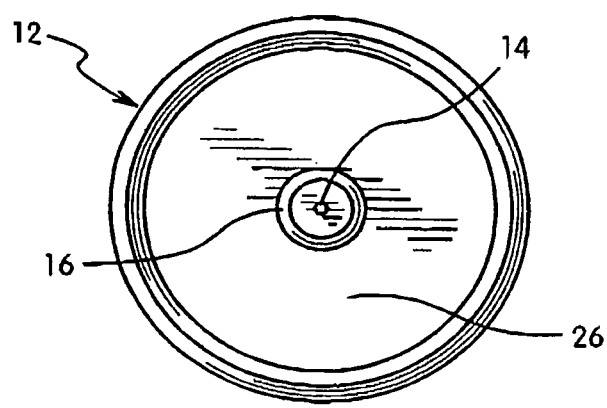
FIG. 3A is a top view of the single microneedle hub assembly of FIG. 1.

A diagram of an exemplary hub assembly 10 in accordance with an embodiment of the present invention is shown in FIG. 1A. For the following discussion, reference will be made to FIGS. 1A-1B, 2A-2D, and 3A-3B, and as necessary, attention will be drawn to a particular figure. FIGS. 1A and 1B are views illustrating an example of a single microneedle hub assembly according to an embodiment of the present invention. FIG. 1A is a perspective view, and FIG. 1B is a side view in cross section of the hub assembly. FIGS. 2A-2D are views illustrating an example of a multiple microneedle hub assembly according to an embodiment of the present invention. FIG. 2A is a perspective view, FIG. 2B is a first top view in cross section, FIG. 2C is a second top view in cross section and FIG. 2D is a side view in cross section of the multiple microneedle hub assembly. FIGS. 3A and 3B are top views illustrating an example of both a single and a multiple microneedle hub assembly.

FIG. 1A is a view illustrating an example of a single microneedle hub assembly 10. In the assembly of FIG. 1A, the hub assembly includes a cylindrical housing 24 extending between a flat patient contact surface 26 (or "frontend"), and a cylindrical open end 30 (or "backend") provided to engage a pen device. The hub assembly includes a backend member 22, such as a needle, and mounting threads 28 within an engagement opening 30 on the needle hub housing 24. Although mounting threads are shown in the assembly 10 of FIG. 1A, other embodiments can use alternate engagement mechanisms, such as a luer lock mechanism. The contact surface 26 includes a single microneedle 14 protruding beyond a depth limiting post and support hub 16 that extends from the contact surface 26. The microneedle 14 is firmly held within the depth limiting post and support hub 16 via an adhesive 18 contained within a recess defining an adhesive reservoir. Although an adhesive reservoir is shown in FIG. 1A, the hub assembly body may be manufactured wherein the microneedle 14 is held in place by the contact surface 26 material.

A raised skin tensioning member, or ring 12, is located about the contact surface circumference as shown in FIG. 3A. The tensioning ring 12 extends above the contact surface 26 to a height in some proportion to the limiting post and support hub 16, allowing skin tensioning around the microneedle 14. Although the embodiment shown in FIG. 1A shows the tensioning ring 12 and the limiting post and support hub 16 having equal heights, still other embodiments can have tensioning rings, limiting posts and support hubs of unequal heights as required for effective skin tensioning.

The microneedle 14 can include any number of needle gauges, lengths and construction, however, needle gauges less than or equal to 30 gauge (nominal size specification of less than or equal to 0.012 in. outer diameter and 0.004 in. inner diameter) are typically used. The microneedle length is preferably between about 0.3 mm and about 5.0 mm depending upon application. For example, lengths of between about 0.3 and about 2.0 mm are used for intradermal delivery, and lengths between about 2.0 and about 5.0 mm are used for shallow subcutaneous delivery. These values may slightly overlap due to biological variables such that microneedle lengths slightly less than 2.0 mm may be used shallow subcutaneous delivery, and microneedle lengths slightly greater than 2.0 mm may be used for intradermal delivery. The microneedles can include a number of materials, such as stainless steel, silicon or silicon compounds, polymers or plastics. Alternatively, a microneedle pen can utilize larger gauge cannula with appropriate length and bevel characteristics to still maintain accurate fluid instillation to the intradermal space without topical deposition to the skin surface.

As shown in FIG. 1B, the microneedle 14 is seated within the adhesive reservoir 18 and creates an open flow channel between the exposed end of the microneedle 14 located above the contact surface 26, and an internal opening 32 adjacent to an exposed end of a backend member 22, typically a larger needle such as a 31 gauge needle. In use, pen needle hub assemblies as shown in FIGS. 1A and 2A incorporate a backend needle to contact a cartridge within the pen device housing. The backend needle 22 is required to penetrate the drug cartridge and create a flow path between the drug cartridge and the patient contact surface with minimum resistance to fluid flow. The drug cartridge typically includes a septum seal for contact with the backend needle, and a stopper at an opposite end. The cartridge can be configured to provide multi-dose or single dose medication, or substance flow, and can be a single component cartridge (i.e. sealed elastomeric tube or ampoule) or a multi-component cartridge (i.e. for in situ reconstitution of unlike phases or for separate containment of unlike drugs). Various drug formulations can be used with the cartridge, such as aqueous liquids or solutions, particulate or colloidal suspensions, emulsions, gels, creams, pastes, dry solids and so forth. These various drugs can include peptides, proteins, small organic and inorganic molecules, nucleic acids, or vaccines.

Proper operation of the pen device requires the backend needle 22 of the hub assembly 10 in FIG. 1A to be sufficiently strong enough to penetrate the elastomeric septa of the drug cartridge without bending or deflection. The backend needle 22 must also include a sufficient inside diameter to allow good volumetric flow after penetrating the cartridge. However, the simple substitution of a long 34 gauge needle as an extension of the microneedle 14 of the embodiment shown in FIG. 1A would result in a high probability that the backend needle 22 would bend during use. Such bending of the backend needle would reduce the flow path due to the decreased section modulus of the needle, as compared to current 29-31 gauge needles. Also, as resistance to flow within the needle is proportional to cannula length and radius to the fourth power, a long 34 gauge needle serving as both frontend and backend needle would generate excessive backpressure and resistance to flow of a substance from the pen body to the intradermal space.

Therefore, the embodiment of assemblies 10 and 40 shown in FIGS. 1A and 2A include a larger diameter backend needle, typically of a gauge ≥31, to penetrate the drug cartridge. For example, the backend needle, or piercing portion of the backend needle (where a single, reduced diameter needle is used) may be 29, 30 or 31 gauge. In FIG. 1A, the larger penetrating needle 22 increases mechanical strength and decreases resistance to flow between the cartridge and the microneedle 14 delivering the substance to the intradermal space. The larger cannula used for the backend needle 22 serves to direct fluid flow into and through the microneedle 14 pathway via the internal opening 32. Although a cannula is shown as the backend needle 22 in the assembly 10 of FIG. 1 and needle 42 of FIG. 2, other embodiments can include a housing 24 modification having a molded or formed plastic tube in place of the cannula, of sufficient strength to penetrate a rubber septum of a drug cartridge. The use of a tube instead of a cannula can have some benefit both from a manufacturing and safety standpoint. Alternatively the microneedle 14 and backend needle 22 could be combined as a single tapered, or otherwise reduced diameter (e.g. necked down) needle thus eliminating space 32. Such a needle would have sufficient cartridge penetrating strength and fluid flow and still offer effective microneedle targeting.

In both FIGS. 1A and 2A, the frontend of the pen needle system must have sufficient ability to allow the flow of fluid when used both in vitro, for checking flow accuracy and priming, and when used in vivo, for accurate drug dosing. As stated above, resistance to flow within the needle is proportional to cannula length and radius to the fourth power. A single 34 gauge needle 14 at the frontend, having a 1 mm exposed length, can significantly increase the time required to expel a given substance dose of 5-25 units (U) of insulin or other medicament (equivalent to 50-250 microliters of fluid). However, an array of microneedles in place of the single microneedle 14, such as an array of three 34 gauge needles, each with a 1 mm exposed length as shown in FIG. 2A, has a similar dosing time duration as existing subcutaneous systems when delivering against atmospheric pressure. The performance of the microneedle array is explained by noting that the cross-sectional area of three 34 gauge needles is nearly equivalent to the cross-sectional area of a single 31 gauge stock needle.

When a microneedle system is used for in vivo delivery, such as delivery to an intradermal space, a significant backpressure is encountered due to instillation rate of fluid volume into an essentially sealed or closed space having limited distensibility. This is true even though intradermal delivery of substances, such as medications involve much smaller volumes of liquid, 100 microliters for example, as compared with the volumes used in subcutaneous systems, which can be as large or larger than 500 microliters. The magnitude of backpressure is also proportional to both the instillation rate as well as the volume. This level of pressure is not typically encountered when delivering a substance to the subcutaneous space, which is generally regarded as a region of highly compressible or distensible tissue with a much higher limit for instilled fluid volume. By utilizing a multi-port frontend hub assembly, as shown in FIGS. 2A and 3B, the relative delivery rate and volume delivered through each microneedle in the array is reduced, resulting in an improved in vivo dosing process.

As noted earlier, intradermal delivery via a single 34 gauge microneedle, as shown in FIGS. 1A and 3A, can be difficult in some applications, requiring a higher level of pressure and an extended delivery period relative to the pressure and time required for subcutaneous delivery. In vivo delivery via a multineedle microarray requires substantially less pressure to expel a dosage, and is more rapid. Therefore, another embodiment of the present invention shown in FIG. 2A utilizes a multineedle front end hub assembly, having two or more individual microneedles substantially the same as described above for FIG. 1A. Other aspects to decrease the pressure differential for delivery to the intradermal space can also be considered.

FIG. 2A is a view illustrating an example of a multiple microneedle hub assembly 40. In the assembly of FIG. 2A, the hub assembly includes a cylindrical housing 44 extending between a flat patient contact surface 60, and an open end 62 provided to engage a pen device, substantially as described for FIG. 1A. The contact surface 60 includes three microneedles 50a, 50b and 50c, each protruding about 1 mm beyond individual depth limiting posts and support hubs 52a, 52b and 52c, surrounding each microneedle respectively. Each microneedle 50 is held in place via an adhesive reservoir 56a, 56b and 56c substantially as described above for microneedle 14 in FIG. 1A. As shown in FIG. 2B, a multi-port flow channel 58 is formed that allows fluid communication between the microneedles 50 and the backend needle 42 substantially as described for the internal opening 32 of FIG. 1B.

A skin tensioning member, or ring 54, discussed in more detail below, is located about the circumference of the surface 60, and about each limiting post and support hub 52, as shown in FIG. 3B. The tensioning ring 54 extends above the contact surface 60 to a height proportional to the limiting post and support hubs 52, allowing skin tensioning around each microneedle 50. Although the embodiment shown in FIG. 2A shows the tensioning ring 54 and the limiting post and support hubs 52 having equal heights, still other embodiments can have tensioning rings, limiting posts and support hubs of unequal heights as required for effective skin tensioning.

As stated earlier, a significant backpressure is encountered during drug placement due to instillation rate and fluid volume placement into an essentially sealed or closed space. In another embodiment of the present invention, these pressure differentials can be further decreased by the use of microneedles of different lengths in FIGS. 1A and 2A. Shorter needles, such as those between 0.3 and 0.5 mm, can access the tissue plane between dermis and epidermis, which upon fluid instillation can physically separate to provide a larger available fluid volume space and thereby reduce backpressure. This however can have negative implications, such as difficulty in maintaining the tissue interface, excessive leakage, or could lead to tissue damage resulting in epidermal necrosis. For example, 34 gauge needle systems of 1.0 mm length accurately target the dermis, but at a tissue depth which has limited distensibility. The pharmacokinetics and pharmacodynamic benefits and changes for drug delivery to this tissue space have been previously disclosed. Slightly longer needles, such as those between 1.7 and 5.0 mm target a deeper tissue space, closer to the hypodermic junction, and referred to herein as the shallow subcutaneous space. Since this space is closer to a tissue plane between the dermis and the true subcutaneous space, it allows better fluid diffusion between the tissue planes resulting in less tissue backpressure. However, the relative effects of this deeper delivery on tissue pressure and also on the pharmacokinetics and dynamics of drug uptake and distribution can be slightly less favorable than true intradermal delivery. Therefore the embodiments of FIGS. 1A and 2A encompass needle lengths of between about 0.3 to about 5.0 mm. Embodiments having needle lengths of between about 0.75 and about 1.7 mm assure intradermal delivery, and embodiments having microneedle lengths of between about 1.7 and about 5.0 mm allow for delivery to the shallow subcutaneous region.

Additional features, beyond needle specifications, can assist in providing appropriate and efficient penetration of the pen microneedles. The embodiments shown in FIGS. 1A and 2A utilize skin tensioning members, such as a post and ring configuration on the array face which allows both tensioning of the skin and prevention of interference with the wheal which results from intradermal fluid instillation. This serves to increase skin tension to aid insertion and minimizes pressure on the direct site of fluid instillation. FIGS. 3A and 3B show the skin tensioning aspects of the hub assemblies for FIGS. 1A and 2A in greater detail.

FIG. 3A is a top view illustrating an example of a single microneedle hub assembly as described in FIG. 1A, and FIG. 3B is a top view illustrating an example of a multiple microneedle hub assembly as described in FIG. 2A, each view illustrating the skin tensioning members of the hub surfaces. In FIGS. 3A and 3B, the hub assemblies comprise an essentially planar surface which is recessed relative to the raised skin tensioning components.

In the single needle embodiment shown in FIG. 3A, the microneedle 14 is surrounded by a depth limiting post 16 which acts as a support for the microneedle structure. A perimeter tensioning ring 12 is positioned around the periphery of the microneedle hub. The relative heights of the depth limiting post 16 and tensioning ring 12 can be varied to obtain the desired tensioning and depth properties, but are typically of the same height.

The top view of the hub assembly of FIG. 2A, which is shown in FIG. 3B, is formed in a fashion similar to FIG. 3A. As in the single needle embodiment of FIG. 3A, each microneedle 50 of FIG. 3B is surrounded by a depth limiting post 52 that also acts as a support for the microneedle. A skin tensioning ring 54 is positioned around the periphery of the hub and each microneedle. Both the depth limiting posts 52 and the skin tensioning ring 54 are elevated relative to the planar surface 60 of the hub. As shown in FIG. 3B, the tensioning ring 54 in the multineedle array embodiment can also include a series of structural elements acting in concert to tension the surface for insertion of the microneedles. Also, the relative heights of the depth limiting posts and tensioning rings can be varied to obtain the desired tensioning and depth properties.

Figure 6A:
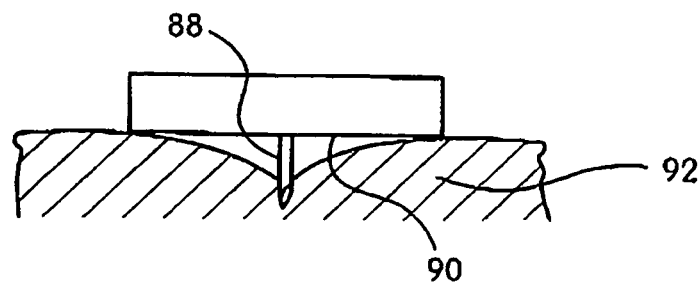
FIG. 6A is a side view in partial cross section illustrating substance delivery pen use where a skin tensioning member is lacking.
Figure 6B:
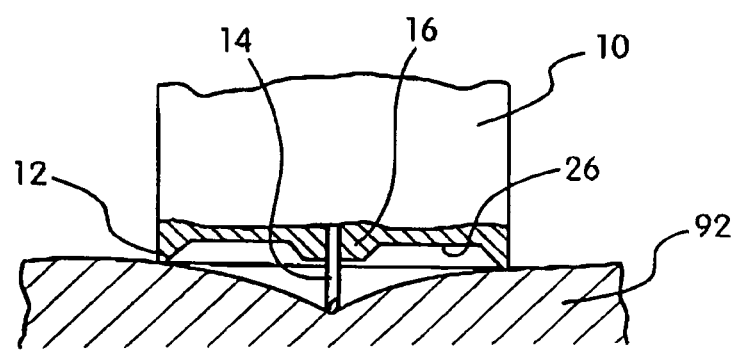
FIG. 6B is a side view in partial cross section illustrating substance delivery pen use where the skin tensioning member of FIG. 1A is present.
Figure 6C:
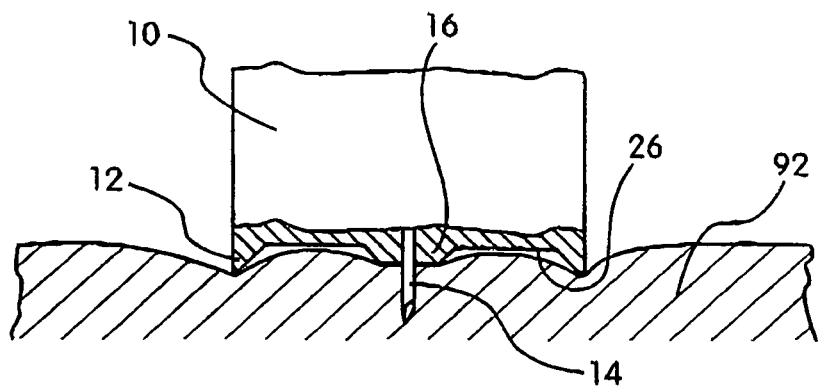
FIG. 6C is a side view in partial cross section illustrating completed substance delivery pen use where the skin tensioning member of FIG. 1A is present.

The skin tensioning members of FIG. 3A are explained further in FIGS. 6A-6C. FIG. 6A is a side view in partial cross section illustrating substance delivery pen use where a skin tensioning member is lacking. FIGS. 6B and 6C are side views in partial cross section illustrating substance delivery pen use where the skin tensioning members of FIG. 1A are present.

In FIG. 6B, when the hub assembly 10 makes contact with a patient surface 92, such as skin, the skin tensioning ring 12 contacts the surface shortly after the microneedle 14 begins to deform the surface prior to penetration. As shown further in FIG. 6C, the ring 12 minimizes deformation of the surface, allowing greater accuracy in microneedle penetration. The skin surface 92 contacts the post 16, which limits insertion depth. As shown in FIG. 6A, microneedle insertion where a tensioning member is lacking results in greater deformation of the surface 92, creating poor microneedle insertion and inaccurate tissue depth targeting.

Other methods of skin tensioning can be incorporated as an alternative to the ring and post system described above. Such methods of skin tensioning can include transiently applying a brief initial vacuum to the injection site, manually or mechanically pulling or stretching the skin, or utilizing a mechanically controlled rapid insertion. For example, ballistic inserters result in brief inertial stiffening of the skin, reducing effective elasticity. These mechanisms can be used either singularly or in combination, or with other techniques readily known to those skilled in the art.

Figure 4:
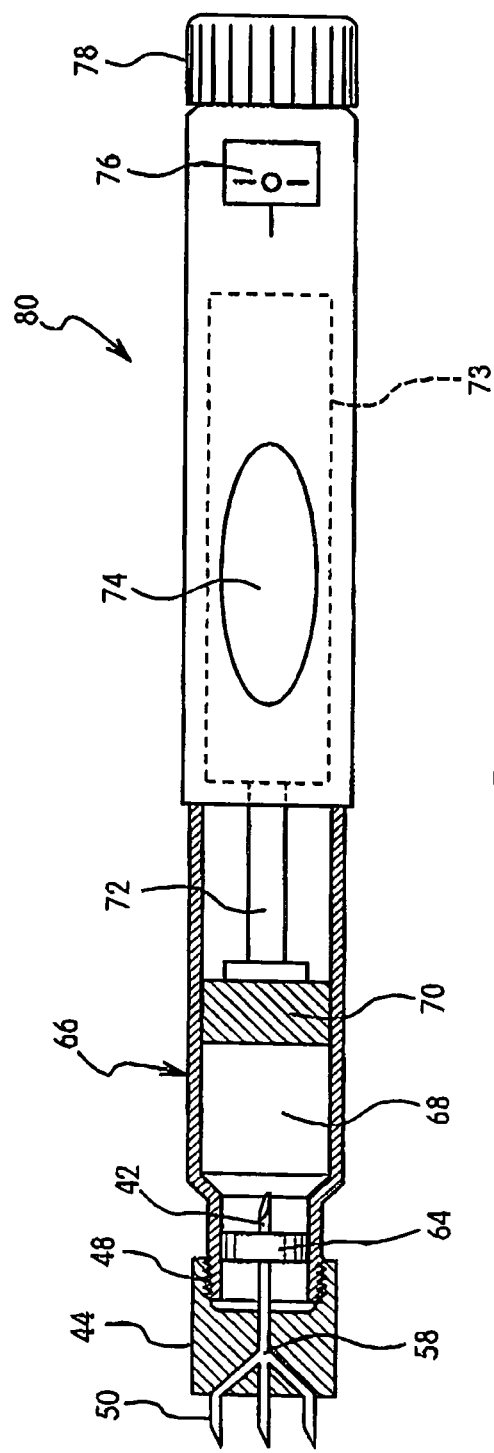
FIG. 4 is a side view in partial cross section illustrating a substance delivery pen according to one embodiment of the present invention.

FIG. 4 is a view illustrating an example of a drug delivery pen device 80 utilizing a multineedle hub assembly as described in FIGS. 2A-2D and 3B. FIG. 4 is a side view in partial cross section illustrating a substance delivery pen according to one embodiment of the present invention, and FIGS. 5A and 5B are views illustrating a second embodiment wherein the patient contact surface is at a reduced angle relative to the device centerline.

As shown in FIG. 4, an array of microneedles 50 are incorporated into a hub assembly 44 removably engaged with a pen device body 66. As noted above, the engagement can be achieved using threaded connections 48 on the hub assembly 44, adapted to mate with like threaded connections located on the pen device body 66, however, this is only one example of an engagement means between hub assembly and pen device body. A luer fitting or snap fit fitting can also be used.

FIG. 4 shows an embodiment having an array of three microneedles, however, as shown in FIG. 1A, a single microneedle can be used. In still other embodiments, a hub assembly can be used which includes 2, 4 or more microneedles, as required by the particular application. In each case, a fluid pathway 58 is contiguous with the microneedles 50 and is contained within the microneedle hub assembly 44. A cartridge piercing member, or in this example, a backend needle 42, is contained within the microneedle hub assembly 44 within the engagement opening.

In use, a cartridge 68 is located within the delivery pen device 80 and contains a substance to be dispensed. At the end of the cartridge opposite the septum 64, a drug cartridge stopper 70 is in communication with a plunger 72, slidably engaged within the pen body 66 and driven by a known type of drive mechanism 73. The backend needle 42 pierces the drug cartridge septum 64 when the hub assembly 44 is engaged with the pen body 66. The drive mechanism 73 is activated via an external user interface 74, which then causes the plunger 72 to exert a force on the stopper 70. This force moves the stopper 70 within the cartridge 68, forcing the contents of the cartridge toward the exposed end of the backend needle 42, into the fluid pathway 58 and out through the microneedles 50.

Since the in vivo biomechanical requirements for delivery into the intradermal space are significantly different than those for delivery to the subcutaneous space, the physical and mechanical components and mechanisms of pen delivery systems must be considered to insure effective dosage delivery. Particular modifications of the pen structure itself are dictated by the extremely high backpressures generated upon intradermal instillation of even small volumes of fluids.

In particular, systems or components that have the potential for elastomeric compression are not suitable for the microneedle pen systems of FIGS. 4 and 5. As shown in FIG. 4, cartridge 68 including a rubber stopper 70 can result in weeping of non-negligible fluid volume from the pen needles 50 after removal from the biological system. This is an indication of elastomeric compression of the rubber stopper 70 of the cartridge 68 during use. While in communication with the body and high-pressure bleb, the rubber stopper 70 can become compressed. Upon removal from the body and with the concomitant elimination of backpressure, the stopper 70 relaxes against the reduced pressure of the atmosphere and ejects additional fluid contents. In the embodiment shown in FIG. 4, this effect is eliminated by utilizing a stopper 70 prepared from polymeric systems such as polytetrafluoroethylene, nylon, other rigid plastics or other materials which have reduced compressibility. This and other modifications to the cartridge 68 are important for reducing compressibility of components and flex in the cartridge walls under fluid pressure on the fluid bed. Still other modifications to reduce compressibility include altering the septum materials, cartridge walls, and cartridge materials.

As force per unit area is decreased for larger drug vials or cartridges, a minimal cross sectional cartridge area is preferred for microneedle pen systems as described above. Microneedle pen embodiments typically utilize 1.5 ml insulin-type cartridges, rather than the 3.0 ml versions which are used in other applications. A single unit dose pen for intradermal systems benefits by providing a small diameter dosing cartridge typically having a longer length than larger diameter cartridges. This improves compressive force levels on the fluid bed due to the reduced cartridge cross-sectional area and allows accurate volume quantitation in a manner similar to small volume microliter syringes. Therefore the embodiments of FIGS. 1A, 2A, 4 and 5 utilize a cartridge with significant force/unit area, preferably through a narrow diameter bore, with extended length for volume accommodation.

Additionally, the plunger 72 of the pen device 80 is constructed of a non-compliant and non-compressible material. The material is sufficiently resilient to communicate an appropriate force from the actuator to the stopper 70, however, the plunger 72 will not bend nor tend to be compressed along its axis, leading to "shortening" under the pressures required for operation of the pen. In addition, the end of the plunger 72 in communication with the stopper 70 exerts a substantially even force on the stopper 70 during operation, and prevents leakage from the cartridge around the sides of the stopper or plunger. Suitable materials that fit these requirements include polymeric materials such as rigid plastic materials, and metallic materials such as stainless steel. Additional pen component materials can include metals, plastics, ceramics, and so forth.

Effects of increased pressure also translate to the body and mechanical components of the pen drive mechanism 73, which are also constructed of polymeric components in most current pen devices. For effective delivery, the drive mechanism components must have sufficient strength to translate these forces to the drug reservoir and also to withstand forces translated backward to prevent breakage, malfunction, or other failure. Therefore appropriate materials choices are also necessary in the drive mechanism 73. Typical pen drive mechanisms 73 include circular drive screws, linear drive screws, ratcheting drives, and stored kinetic energy, such as mechanical spring or air pressure.

In the embodiment shown in FIG. 4, the use of a stiffer stopper 70 reduces the tendency of the system 64 to "drool" when used in vitro against atmospheric pressure as described above. However, during in vivo usage, pen systems tend to "lock up" near the end of the delivery and fail to fully advance the drive mechanism which serves to expel the substance from the cartridge 68. In such cases, after the device 80 is removed from contact with the patient, the plunger 72 may then be fully depressed to express the remaining 1-2 U (10-20 microliters of volume). This again reflects the potential for compression of elastomeric parts and the need for a more linear drive mechanism, with very positive detents. When used with microneedle hub assemblies, driving mechanisms with linear or direct drives perform better than rotary drives, however linear drives can be more difficult to depress. However, once locked at the end of dose, these drives are easy to maintain in place. Drive mechanisms which are not actuated with user force but utilize stored energy can also be used, and provide better ease of use. Optimum results can be achieved using drive mechanisms which include a ratcheting mechanism with positive locking at each dosing increment and an end of dose lock.

As stated above, embodiments of the present invention can incorporate a drive mechanism with minimal elastic compliance of all parts, either singly or together. Other embodiments can incorporate drive mechanisms having well-defined stops, steps or ratchets at each dosing increment to insure dose accuracy. These stops enable ease of use by "locking" the drive in an advanced position, which is especially important to signal end of dose. Still other embodiments utilize a linear or other driving force that confers a significant mechanical advantage when actuated by thumb pressure, or other force generated by the user. Additional embodiments can utilize a mechanical force that can be actuated and forgotten, such as a spring, having a readable gauge to signal end-of-dose.

For embodiments having cartridges that store multiple doses, a unit dose counter 76 can also be incorporated into the device 80 in FIG. 4. Also, a mechanism 78, giving the user the ability to adjust the dosage size, can also be included. For example, under certain conditions it may be desirable to administer multiple unit doses of a particular medication. An example of this is in diabetes where, depending upon glucose levels in a patient, variable amounts of insulin would be administered. In these embodiments, a dial located on the mechanism 78 for metering doses can be incorporated into the device 80.

With most currently manufactured pen screw drive systems, physical force is applied to the top of the pen to drive an advancing screw. This increases the tendency to push down on the device during use. Reducing downward force levels may be achieved in a number of ways. One solution to eliminate excessive downward force utilizes a user actuated mechanical drive to expel the fluid contents. Another solution utilizes a modified patient contact surface angle.

In one embodiment of the present invention, a user actuated mechanical drive releases stored kinetic energy that is generated in the pen mechanism in a separate step prior to actuation, such as the use of a mechanical spring to actuate fluid flow. The low force spring in the device is able to effectively deliver fluid through both single and multineedle microarrays when used in vitro. Other mechanical means include air pressure generated mechanically, chemically or electromechanically. Mechanical drive systems that have efficient force amplification, such as altering the drive ratio of circular gear drives for physically applied pressure, such as thumb pressure, can also be used.

As described above, pressure generated directly at the site of fluid instillation is another issue unique to microneedle delivery systems that must be considered in the design and manufacture of microneedle pen devices. When tissue immediately above or around the intradermal instillation site is compressed, the already high tissue pressure is increased. This can lead to leakage along the microneedle track, either during administration with needles in situ in tissue, or post administration along the tissue track. In pen based systems, this effect is further exacerbated since the user is trying to maintain a perpendicular orientation of the device to the skin, maintain intimate contact of the microneedles in the tissue, and exert a downward force on the screw drive of the pen to expel the fluid or drug. This effect may be reduced or eliminated by the post and ring components of FIGS. 1A, 2A, 3A and 3B, which reduces the area on the pen face in direct compression of the tissue.

Additional reduction of the adverse effects due to excessive pressure can be achieved by angling the patient contact surface of the pen head relative to the axis of the pen device with an offset angle of 0-90 degrees. This reduces the tendency to press too firmly against the tissue face and therefor reduces tissue compression forces. An example of an embodiment of the present invention in which the contact surface of microneedle hub assembly is no longer perpendicular to the center axis of the pen device is shown in FIGS. 5A and 5B.

FIG. 5A shows another embodiment of the drug delivery pen according to the present invention having an angle of disposition of the microneedles with respect to the pen body. The pen body 66, including the drug cartridge 68 and cartridge septum and cap 64 are substantially as described above for FIG. 4. Therefore, the advantages of this embodiment are realized without further modification to the drug delivery pen itself, but by modification of only the microneedle hub assembly housing.

In the hub assembly 82 of FIG. 5A, the assembly includes a cylindrical housing 84 extending between a inclined patient contact surface 86, and an open end shown engaged with a pen device, substantially as described for FIG. 4. The contact surface 86 includes three microneedles 50a, 50b and 50c, each protruding beyond individual depth limiting posts and support hubs, surrounding each microneedle respectively. Each microneedle 50 is held in place via an adhesive reservoir, and a multi-port flow channel 58 is formed that allows fluid communication between the microneedles 50 and the backend needle 42 substantially as described above. The angling of patient contact surface relative to the axis of the pen device reduces the tendency to press too firmly against the tissue face while activating the device, serving to effectively reduce tissue compression forces. FIG. 5B shows the orientation of the microneedles on the patient contact surface 86 of FIG. 5A. Although microneedles 50a, 50b and 50c are shown in a linear orientation along the patient contact surface 86 in FIG. 5B, other embodiments can include alternate microneedle orientations. For example, the microneedle orientation as shown in FIG. 3B can also be used.

The embodiments described above for a microneedle based pen system for effective drug delivery to the intraepidermal, intradermal, or shallow subcutaneous (hypodermis) space include features such as a sufficiently open fluid paths to allow ready transport of the liquid or suspension from the cartridge reservoir to the microneedle inlet without requiring excessive pressure or occlusion. Also included is a biological interface composed of one or more hollow cannula which can penetrate the stratum corneum, and accurately access the desire tissue depth in skin or in the proximity of skin, and transmit a desired fluid volume through the body of the interface into the specified or targeted tissue space both accurately, with no fluid loss out of tissue to surface or to untargeted tissue, and efficiently, in a manner that is amenable to the device user and recipient.

Other features include a fluid driving mechanism that can overcome the high pressures inherent for fluid delivery to the dermal or near dermal space. A device mechanism, components, and assembly process is provided which withstands the additional physical forces, such as pressure and compression, inherent in the fluid delivery to the targeted tissue space. The device mechanism and configuration which is easily activated by the user to deliver the fluid to the targeted tissue space, can be maintained in an orientation or configuration for a sufficient time period to accomplish the delivery. The delivery pen system described above serves to reduce pain due to instillation, provide better access to the desired tissue space, and provide better or beneficially altered drug pharmacokinetics or pharmacodynamics.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A substance delivery device, comprising:
a supply housing having an outlet;
a single cartridge in said supply housing containing a substance and having a septum at a first end and a stopper having a distal face at a second end to seal said cartridge, said stopper having a proximal face being positioned to engage a plunger having a distal face;
a hub housing having a proximal end and a distal end, said distal end having a skin contact surface and at least one microneedle extending from said skin contact surface, said proximal end removably coupled to said outlet of said supply housing and having a piercing member oriented to pierce said septum, said piercing member mounted to said hub housing so as to be removable therewith, said at least one microneedle having a length suitable for intradermal or shallow subcutaneous delivery of said substance, said microneedle being separate, and spaced, from said piercing member, said microneedle being in fluid communication with said piercing member for receiving said substance from said cartridge, a fluid flow path is defined through said hub housing, said microneedle defining the narrowmost portion of said fluid flow path; and a drive mechanism located within said supply housing for moving said plunger and said stopper, wherein the distal face of said stopper moves a substantially equivalent distance to the distal face of said plunger toward said septum, said septum being substantially free of deflection to dispense said substance from said cartridge through said piercing member to said at least one microneedle for delivering said substance to a patient, wherein said skin contact surface further comprises a depth limiting post to support and limit a depth of insertion for said microneedle, said post formed about said microneedle and extending above said skin contact surface.

2. A substance delivery device as claimed in claim 1, wherein said depth limiting post includes an axial dimension and an outer face, and wherein said microneedle extends axially from said outer face.

3. A microneedle delivery device as claimed in claim 1, wherein said depth limiting post has a height above said skin contact surface and a width sufficient to allow substantially complete penetration of said microneedle.

4. A substance delivery device as claimed in claim 1, wherein said skin contact surface further comprises a tensioning ring to tension patient skin during insertion of said microneedle, said ring comprising a ridge raised from said skin contact surface and concentrically located about said microneedle.

5. A substance delivery device as claimed in claim 4, wherein said tensioning ring extends from said contact surface a height of less than or equal to said height of said depth limiting post.

* * * * *